(12) United States Patent
Hu et al.

(10) Patent No.: US 10,701,907 B2
(45) Date of Patent: Jul. 7, 2020

(54) METHOD FOR PRODUCING YY SUPER-MALE AND XY PHYSIOLOGICAL FEMALE COMMON CARPS

(71) Applicant: Institute of Hydrobiology, Chinese Academy of Sciences, Wuhan, Hubei (CN)

(72) Inventors: Wei Hu, Wuhan (CN); Mouyan Jiang, Wuhan (CN); Yongming Li, Wuhan (CN); Binbin Tao, Wuhan (CN); Ji Chen, Wuhan (CN); Zuoyan Zhu, Wuhan (CN)

(73) Assignee: Institute of Hydrobiology, Chinese Academy of Sciences, Wuhan (CN)

( * ) Notice: Subject to any disclaimer, the term of this patent is extended or adjusted under 35 U.S.C. 154(b) by 248 days.

(21) Appl. No.: 15/870,334

(22) Filed: Jan. 12, 2018

(65) Prior Publication Data

US 2018/0317459 A1 Nov. 8, 2018

(51) Int. Cl.

| | | |
|---|---|---|
| *A01K 67/027* | (2006.01) | |
| *C12N 15/00* | (2006.01) | |
| *A01K 61/17* | (2017.01) | |
| *C12N 15/01* | (2006.01) | |
| *A61K 31/565* | (2006.01) | |
| *A61D 19/02* | (2006.01) | |
| *A01K 61/95* | (2017.01) | |
| *A01K 61/80* | (2017.01) | |
| *A61K 31/167* | (2006.01) | |

(52) U.S. Cl.
CPC .............. *A01K 61/17* (2017.01); *A01K 61/80* (2017.01); *A01K 61/95* (2017.01); *A01K 67/027* (2013.01); *A61D 19/02* (2013.01); *A61K 31/167* (2013.01); *A61K 31/565* (2013.01); *C12N 15/01* (2013.01); *A01K 2207/35* (2013.01); *A01K 2217/03* (2013.01); *A01K 2227/40* (2013.01); *A01K 2267/02* (2013.01); *Y02A 40/812* (2018.01)

(58) Field of Classification Search
CPC .. A01K 67/027; A01K 61/95; A01K 2207/35; A01K 2227/40; A01K 2267/02; C12N 15/01; A61D 19/02
See application file for complete search history.

(56) References Cited

PUBLICATIONS

Zambrano et al., "Invasive potential of common carp (*Cyprinus carpio*) and Nile tilapia (*Oreochromis niloticus*) in American fresh water systems," Can. J. Fish. Aquat. Sci., 63: 1903-1910 (2006).
Chapman, "Invasive Asian Carps in North America," American Fisheries Soceity Symposium 74, Proceedings of the Symposium, Invasive Asian Carps in North America: A Forum to Understand the Biology and Manage the Problem, Held in Peoria, Illinois, USA on Aug. 2006, published 2011.
Weber et al., "Relationships among invasive common carp, native fishes and physicochemical characteristics in upper Midwest (USA) lakes," Ecology of Freshwater Fish, 20:270-278 (2011).
Forsyth et al., "Population dynamics of invading freshwater fish: common carp (*Cyprinus carpio*) in the Murray-Darling Basin, Australia," Biol. Invasions, 15:341-354 (2013).
Bajer et al., "Effects of common carp on phosphorus concentrations, water clarity, and vegetation density: a whole system experiment in a thermally stratified lake," Hydrobiologia, 746: 303-313 (2015).
Vilizzi et al., "Experimental evidence from casual criteria analysis for the effects of common carp *Cyprinus carpio* on freshwater ecosystems: a global perspective," Reviews in Fisheries Science & Aquaculture, 23:3, 253-290 (2015).
Bajer et al., "Biological invasion by a benthivorous fish reduced the cover and species richness of aquatic plants in most lakes of a large North American ecoregion," Global Change Biology, 22, 3937-3947 (2016).
Luque et al., "The 100th of the world's worst invasive alien species," Biol. Invasion, 16: 981-985 (2014).
Gutierrez et al., "A model describing the effect of sex-reversed YY fish in an established wild population: the use of a Trojan Y chromosome to cause extinction of an introduced exotic species," Journal of Theoretical Biology, 241, 333-341 (2006).
Britton et al., "Managing non-native fish in the environment," Fish and Fisheries, 12, 256-274 (2011).
Vilizzi, "The common carp, *Cyprinus carpio*, in the Mediterranean region: origin, distribution, economic benefits, impacts and management," Fisheries Management and Ecology, 19, 93-110 (2012).
Koehn et al., "Managing flows and carp," Technical Report series, Arthur Rylah Institute for Environment Research, 123 Brown Street, Heideberg, Victoria 3084, Australia (Feb. 2016).
Klassen et al., "Chapter 1.1. History of the sterile insect technique," Sterile Insect Technique. Principle and Practice in Area-Wide Integrated Pest Management, 3-36 (2005).
Twohey et al., "The sterile-male-release technique in great lakes sea lamprey management," J. Great Lakes Res., 29 (Supplement 1): 410-423 (2003).
Wang et al., "Stochastic models for the Trojan Y-chromosome eradication strategy of an invasive species," Journal of Biological Dynamics, 10:1, 179-199 (2015).
Cotton et al., "Control of introduced species using Trojan sex chromosomes," Trends in Ecology and Evolution, vol. 22, No. 9, 441-443 (2007).
Teem et al., "A Trojan Y chromosome strategy for the eradication of invasive fish," Slide presentation (2011).
Parshad et al., "On the well posedness and refined estimates for the global attraction of the TYC model," Boundary Value Problems, vol. 2010, Article ID 405816, 29 pages (2010).

(Continued)

*Primary Examiner* — Valarie E Bertoglio
(74) *Attorney, Agent, or Firm* — Mei & Mark LLP; Manni Li

(57) ABSTRACT

Method for producing YY super-male and XY physiological female common carps, with which YY-chromosome super-male common carp can be cultivated and androgenetic YY super-male common carp is produced, where microsatellite markers are used for paternity testing and test crossing confirmation. The YY common carp is crossed with normal female common carp to produce the progenies of only male common carp, and without sex identification, the juvenile male common carp with known sex are subjected to artificial sex reversal to produce XY physiological female common carp.

4 Claims, 1 Drawing Sheet

Specification includes a Sequence Listing.

(56) References Cited

PUBLICATIONS

Parshad et al., "On the global attractor of the TrojanY chromosome model," Communications on Pure and Applied Analysis, manuscript submitted to AIMS Journals (2011).

Zhao et al., "Existence of global attractor for the Trojan Y chromosome model," Electronic Journal of Qualitative Theory of Differential Equations, No. 36, 1-16 (2012).

Wang et al., "Analysis of the Trojan Y-Chromosome eradication strategy for an invasive species," J. Math. Biol., 68:1731-1756 (2014).

Teem et al., "A comparison of the Trojan Y Chromosome and daughterless carp eradiction strategies," Biol. Invasion, 16: 1217-1230 (2014).

Yamamoto, "Estrone-induced white YY female and mass production of white YY males in the Medaka, *Oryzias Latipes*," Genetics, 55: 329-336 (1967).

Scholz et al., "Hormonal induction and stability of monosex populations in the Medaka (*Oryzias latipes*): expression of sex-specific marker genes," Biology of Reproduction, 69, 673-678 (2003).

Vera Cruz et al., "Feminization of genotypically YY Nile Tilapia *Oreochromis niloticus* L.," Asian Fisheries Sciences, 9, 161-167 (1996).

Mair et al., "Genetic manipulation of sex ratio for the large-scale production of all-male tilapia *Oreochromis niloticus* L.," Canadian Journal of Fisheries and Aquatic Sciences, 54(2): 396-404 (1997).

Liu et al., "Genetic manipulation of sex ratio for the large-scale breeding of YY super-male and XY all-male yellow catfish (*Pelteobagrus fulvidraco* (Richardson))," Mar. Biotechnol., vol. 14, No. 4, 10 pages (2013).

Schill et al., "Production of a YY Male Brook Trout Broodstock for potential eradiction of undesired Brook Trout populations," North American Journal of Aquaculture, 78:1, 72-83 (2016).

Komen et al., "Effects of oral administration of 17 α-methyltestosterone and 17 β-estradiol on Gonadal development in common carp, *Cyprinus carpio* L.," Aquaculture, 78, 349-363 (1989).

SEQUENCE LISTING

```
<160> NUMBER OF SEQ ID NOS: 4

<210> SEQ ID NO 1
<211> LENGTH: 23
<212> TYPE: DNA
<213> ORGANISM: Cyprinus carpio
<220> FEATURE:
<221> NAME/KEY: modified_base
<222> LOCATION: (1)..(1)
<223> OTHER INFORMATION: methylated at 5'

<400> SEQUENCE: 1
aagcattcgt aagcagtgtc atc                                           23

<210> SEQ ID NO 2
<211> LENGTH: 23
<212> TYPE: DNA
<213> ORGANISM: Cyprinus carpio

<400> SEQUENCE: 2
tctgtaacta atgtgccaaa aag                                           23

<210> SEQ ID NO 3
<211> LENGTH: 22
<212> TYPE: DNA
<213> ORGANISM: Cyprinus carpio
<220> FEATURE:
```

```
<221> NAME/KEY: modified_base
<222> LOCATION: (1)..(1)
<223> OTHER INFORMATION: methylated at 5'

<400> SEQUENCE: 3
cactcttacc tttcctgttt gt                                            22

<210> SEQ ID NO 4
<211> LENGTH: 22
<212> TYPE: DNA
<213> ORGANISM: Cyprinus carpio

<400> SEQUENCE: 4
cagttagtta tttgggtttt gc                                            22
```

METHOD FOR PRODUCING YY SUPER-MALE AND XY PHYSIOLOGICAL FEMALE COMMON CARPS

CROSS-REFERENCE TO RELATED APPLICATION

The subject application claims priority on Chinese application no. 201710315756.9 filed on May 8, 2017. The contents and subject matter of the Chinese priority application is incorporated herein by reference.

BACKGROUND OF THE INVENTION

Technical Field

The present invention relates to genetic breeding of aquatic animals, particularly, method for producing YY super-male and XY physiological female common carps.

Description of Related Art

The common carp, *Cyprinus carpio*, is the third most common freshwater cultivated species worldwide, accounting for 11% of all freshwater aquaculture production worldwide. It is worthy of $5.90 billion with an annual global production of 4.2 million metric tons (FAO 2014). However, the common carp is also listed as one of the world's 100 worst invasive species in parts of the Americas, Oceania, and Africa. In the United States, Canada, and Australia, common carp is one of the exotic invasive species severely destroying native aquatic communities and ecosystems.

At present, attempts to eradicate the invasive population of common carp mainly include regulating water levels, purse seine fishing, electric shocking of fish, whole lake poisoning, and other manual removal methods. However, in most cases, using these methods to eradicate the invasive common carp has proven impractical. As demonstrated by the researches on insect controlling and sea lampreys in the Great Lakes, the invasive species can be effectively controlled and eradicated by shifting the sex ratio of the population of the invasive species.

The Trojan Y chromosome (TYC) strategy has been developed, which is designed to alter the sex ratio of a target fish population by reducing the number of females. Using the TYC strategy, a sex-reversed YY female common carp artificially induced based on the YY super-male common carp cultivated artificially have been released into the water environment to compete with the invasive female common carp for spermatozoa to produce only male progeny (MXY), causing the sex ratio of the population of the invasive common carp to be male-dominated severely and finally resulting in 100% male population to lead to the extinction of the invasive common carp population. The TYC strategy has been analyzed and demonstrated by various mathematical models, however, the strategy is only theoretically feasible at this point.

Estrogen-induced sex reversal technique has been shown in a variety of fish, including medaka, Nile tilapia, yellow catfish, and brook Trout. These physiological female fish (FXY) can be viable and develop into fertile individuals, thereby creating conditions for further cultivating the YY super-male fish. However, the feminization of the male common carp using estrogens to obtain sex-reversed XY physiological females has proven inefficient due to the stronger tolerance of the common carp to estrogens.

SUMMARY OF THE INVENTION

The present invention provides a method where YY-chromosome super-male common carp is cultivated and the sperm thereof is used to cross with normal female common carp to produce male only progeny, which is then artificially reversed in sex into the psychological female common carp. The method is useful for fundamental research on sex determination and differentiation of the common carp as well as controlling population of invasive common carp.

An objective of the present invention is to provide an easy and feasible method for producing YY super-male and XY physiological female common carps. To achieve the objective, the present invention provides a method for producing YY super-male and XY physiological female common carps comprising the following steps:

providing eggs of female parent common carp in a cell culture medium, treating the eggs with UV irradiation, artificially inseminating the treated eggs with sperms of male parent common carp to obtain embryos and incubating the embryos in water, identifying androgenetic offspring from the incubated embryos by using molecular marker M1 having SEQ ID NO: 1 and SEQ ID NO: 2 and molecular marker M2 having SEQ ID NO: 3 and SEQ ID NO: 4, and selecting the offspring that only inherit genetic materials from the male parent common carp, cultivating the androgenetic offspring to sexual maturation, selecting and using sperms of the sexually mature androgenetic offspring to fertilize eggs from normal female common carp to obtain test-crossed offspring, cultivating the test-crossed offspring to sexual maturation, and identifying sexes of the test-crossed offspring and obtaining YY super-male common carps, wherein the parents of the test-crossed offspring that are only male common carps are YY super-male common carps.

Further, the method of the present invention contains the step of performing sex reversal treatment on the male test-crossed offspring of the YY super-male common carps to produce XY physiological female common carps.

In the present invention, the eggs of the female parent common carp may be dispersed and suspended in the cell culture medium at a concentration of about 1200 to 1800 eggs per 50 ml cell culture medium.

In the present invention, the eggs may be treated with UV irradiation by using a 30 W UV sterilization lamp with a wavelength of 254 nm at an irradiation distance of 24-28 cm for about 3.5 to 4.5 minutes.

In the present invention, the male test-crossed offspring of the YY super-male common carps may be treated with estrogen and an androgen receptor antagonist to produce the XY physiological female common carps. Preferably, the androgen receptor antagonist is Flutamide.

In the present invention, the sex reversal treatment of the male test-crossed offspring is performed by cultivating the male test-crossed offspring of the YY super-male common carps to 2 months old, feeding the male test-crossed offspring of the YY super-male common carps with a feed mixed with estradiol and Flutamide twice per day for 3 months, feeding the male test-crossed offspring of the YY super-male common carps with a normal feed without estradiol and Flutamide to produce the XY physiological female common carp. The feed concentration of the estradiol is at 200 mg/kg, and feed concentration of the Flutamide is at 200 mg/kg.

In the present invention, the sex reversal treatment may be performed on the male test-crossed offspring at their juvenile stage.

Compared with the current technology, the present invention has advantages and beneficial effects. In the current technology, no technique exists for successfully reversing the sex of the male common carp into the female common carp, because the sex reversal of the common cap is typically performed by feeding hormone-containing feed in the fry stage; however, there is no stable molecular genetic marker available for identifying the sex of the common carp at the fry stage. Therefore, it is impossible to identify the male fry in the fry stage to perform sex reversal treatment. According to the present invention, androgenetic YY super-male common carps are developed and microsatellite markers are used for paternity testing and test crossing confirmation. The YY common carps are crossed with the normal female common carps to produce the progeny of only male common carps, and without the need for sex identification, the juvenile male common carps with known sex are subjected to artificial sex reversal to produce the XY physiological female common carps. The YY super-male common carp cultivated by the method of the present invention can be applied to either controlling the common carp population as exotic species or fundamental researches such sex determination and differentiation of the common carp. The technique for producing the XY physiological female common carp provides references for further developing YY female common carp.

BRIEF DESCRIPTION OF THE SEVERAL VIEWS OF THE DRAWINGS

FIG. 1 shows maps for microsatellite marker identification of offspring with molecular markers, among which.

DETAILED DESCRIPTION OF THE INVENTION AND EMBODIMENT

Figure 1A:
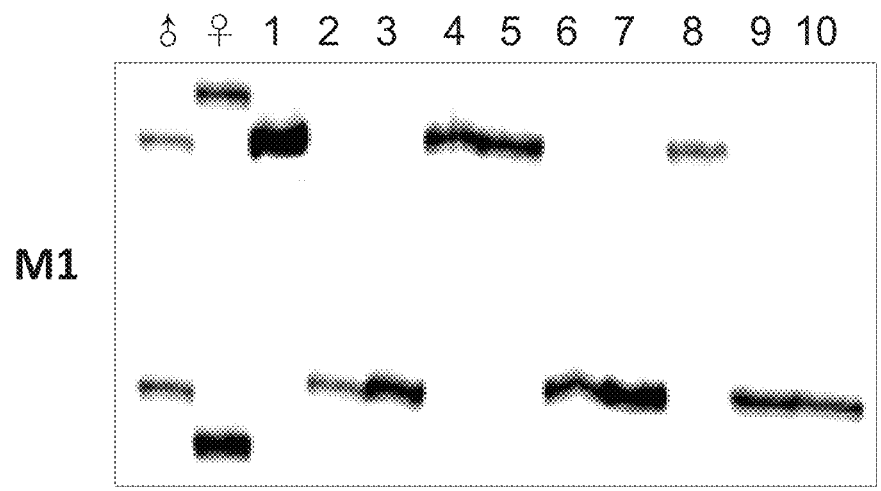
FIG. 1(a) shows the result with the molecular marker M1.

The method of the present invention may be carried out in the following detailed steps:

(1) dispersing and suspending 1200-1800 eggs of the common carp in a 50 mL M-199 cell culture medium contained in a round stainless-steel container having the bottom diameter of 22-28 cm, and placing the container on a standard orbital shake with a speed of 90-110 rpm; and vertically irradiating the eggs using a 30 W UV sterilization lamp with the wavelength of 254 nm at an irradiation distance of 24-28 cm for the irradiation time of 3.5-4.5 min;

(2) after the UV irradiation of the eggs of the common carp, draining the M-199 cell culture medium, adding 0.1-0.3 ml of sperm from the common carp, gently blending uniformly with a piece of dry and clean chicken feather, performing artificial insemination with aerated water at 23-25° C., spreading the eggs on a mesh uniformly, placing the mesh to which embryos of the common carp are attached in a water bath at 40±0.5° C. within 25-35 min after insemination to perform heat shock treatment for 1.5-2.5 min, aerating the treated embryos at room temperature and then incubating the resultant embryos in tap water or pond water;

(3) identifying incubated androgenetic common carp offspring with molecular markers M1 (SEQ ID NO: 1, 5'-mAAGCATTCGTAAGCAGTGTCATC-3' and SEQ ID NO: 2, 5'-TCTGTAACTAATGTGCCAAAAAG-3'), as well as M2 (SEQ ID NO: 3, 5'-mCACTCTTACCTTTCCT-GTTTGT-3' and SEQ ID NO: 4, 5'-CAGTTAGTT-ATTTGGGTTTTGC-3'), and selecting the offspring only inheriting genetic materials (male parent stripes) from the male parents;

(4) cultivating the androgenetic common carp selected in Step (3) to sexual maturation, selecting sexually mature common carp whose sperm can be squeezed artificially, fertilizing eggs from normal female common carp with the sperm to obtain test-crossed offspring; and cultivating the test-crossed offspring to sexual maturation and identifying sexes thereof, wherein parents of which the test-crossed offspring are only male common carp are YY super-male common carps produced through artificially induced androgenesis;

(5) performing sex reversal on the resultant only male offspring (MXY) from the test crossing of the YY super-male common carp (MYY) with estrogen and Flutamide, an androgen receptor antagonist, to produce XY physiological female common carp.

In the method of the present invention, preferably, the method for the sex reversal of the common carp in Step (5) specifically comprises: cultivating the only male offspring (MXY) produced from the test crossing of the YY super-male common carp (MYY) to 2 months old, feeding with feed mixed with estradiol (200 mg/kg) and Flutamide (200 mg/kg) twice a day for 3 months and then with normal feed to produce the XY physiological female common carp.

The advantages of the present invention include:

(1) According to the present invention, no special instrument is needed for making clear of the specific UV dose, the maternal genome can be genetically inactivated by controlling the UV irradiation distance and time, all the reagents and materials used are commercially available, and operators may operate without special research training, therefore, the method is simpler and easier to conduct.

(2) During the UV irradiation, the M-199 cell culture medium and the orbital shaker are used to allow the eggs to favorably disperse and suspend in the medium without activation and moreover, to be irradiated uniformly in a better way, achieving the optimum effect of the genetic inactivation of the maternal genome.

(3) The intensity and duration of the UV irradiation treatment are keys to the genetic inactivation of the maternal genome, however, there will always be some eggs that are not genetically inactivated somehow, as such, there will be normally fertilized ova among the offspring; with the microsatellite markers to possibly distinguish male and female parents and to screen androgenetic individuals, i.e., individuals only inheriting the genetic materials of the male parents, in the offspring population, the cost of subsequent test crossing confirmation can be greatly reduced and the genuine YY super-male common carp can be screened rapidly.

(4) The sexually mature YY super-male common carp is successfully cultivated according to the invention, and it is demonstrated that their test crossing offspring with the normal control female common carp are only males. By directly performing artificial sex reversal on these male fries with known sex, all the resultant female common carp are the XY psychological female common carp, making a breakthrough in the feminization of the male common carp.

Embodiment

In the embodiment of the present invention, production of YY super-male and XY physiological female common carps is conducted with the following steps:

(1) Disperse and suspend 1500 eggs of common carp in a 50 mL M-199 cell culture medium contained in a round stainless-steel container having the bottom diameter of 25 cm, with the M-199 cell culture medium exactly submerging the eggs; place the container on a standard orbital shake (SCILOGEX SK-O180-E) with a speed of 100 rpm; and vertically irradiate the eggs using a 30 W UV sterilization lamp with the wavelength of 254 nm at an irradiation distance of 26 cm for the irradiation time of 4 min (that is, a distance from a light source to the bottom of the container was 26 cm).

(2) After the UV irradiation of the eggs, drain the M-199 cell culture medium, add 0.25 ml of sperm from the common carp, gently mix uniformly with a piece of dry and clean chicken feather, perform artificial insemination with aerated water at 24° C., spread the eggs on a mesh uniformly, place the mesh to which embryos of the common carp were attached in a water bath at 40±0.5° C. within 30 min after insemination to perform heat shock treatment for 2 min, aerate the treated embryos at room temperature and then incubate the resultant embryos in tap water.

Figure 1B:
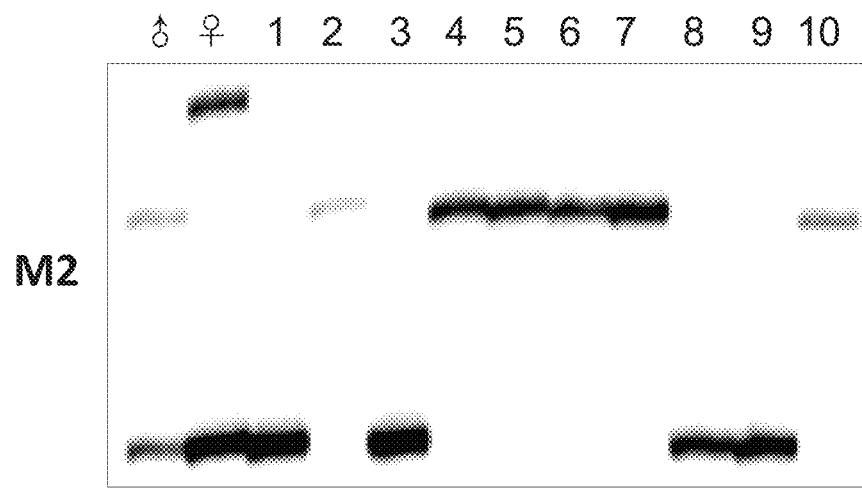
FIG. 1(b) shows the result with the molecular marker M2. In both figures, ♂ denotes male parent; ♀ denotes female parent; electrophoresis lanes 1-10 shows androgenetic offspring only inheriting the genetic information of the male parents.

(3) Cultivate the incubated common carp following a conventional method, and identify the androgenetic offspring of the incubated common carp using molecular markers M1 (SEQ ID NO: 1, 5'-mAAGCATTCGTAAGCA-GTGTCATC-3' and SEQ ID NO: 2, 5'-TCTGTAACTAAT-GTGCCAAAAAG-3') and M2 (SEQ ID NO: 3, 5'-mCACTCTTACCTTTCCTGTTTGT-3' and SEQ ID NO: 4, 5'-CAGTTAGTTATTTGGGTTTTGC-3'), and select the offspring only inheriting the genetic materials (male parent stripes) of the male parents as shown in FIGS. 1(a) and 1(b) of FIG. 1, where a PCR system includes 1 ul of common carp genomic DNA (50 ng/ul), 5 ul of 2×Taq Master Mix, 0.2 ul of each of forward and reverse primers (10 umol/ml), 0.32 ul of M13 fluorescent joint and 3.28 ul of ddH2O. A PCR process consists of pre-denaturation at 94° C. for 3 min, 28 cycles of amplification (denaturation at 94° C. for 30 s, annealing at 56° C. for 25 s and extension at 72° C. for 25 s), and a final extension at 72° C. for 5 min. PCR products were analyzed using the LI-COR 4300 DNA gel electrophoresis system.

(4) Cultivate the androgenetic common carp selected in Step (3) to sex maturation, select sexually mature common carp from which sperm can be squeezed artificially, fertilize eggs from normal female common carp with the sperm to obtain test-crossed offspring. Cultivate the crossed offspring to sexual maturation and identify their sexes, where the male parents of which the crossed offspring were only male common carp were the androgenetic YY super-male common carp.

With the method as described, 25 out of 69 embryos have developed to sexual maturation, with 10 inheriting the genetic information of the male parents, with 4 out of 10 from which the sperm can be squeezed and which has the only male test-crossed offspring.

(5) Cultivate the only male offspring (MXY) resulting from the test crossing of the YY super-male common carp (MYY) to 2 months old according to the conventional cultivation method for the common carp, select 100 fries, and feed them with feed mixed with estradiol (200 mg/kg) and Flutamide (200 mg/kg) twice a day for 3 months and then with normal feed. Till 6 months old, 17 common carp thereamong are detected randomly, with 10 developing with female ovaries, and the 10 common carp have the XY physiological female common carp, with the feminization rate of 58.8%.

The YY super-male common carp cultivated with the method of the present invention can be applied to either controlling of the population of common carp as exotic species or fundamental researches such as sex determination and differentiation of the common carp. The technique for producing the XY physiological female common carp provides references for further developing YY female common carp.

We claim:

1. A method for producing androgenetic YY super-male common carp, comprising:

providing eggs of a single female parent common carp in a cell culture medium, treating the eggs with UV irradiation, wherein the eggs are treated with a 30 W UV sterilization lamp with a wavelength of 254 nm at an irradiation distance of 24-28 cm for about 3.5 to 4.5 minutes, artificially inseminating the treated eggs with sperms of a single male parent common carp and performing a heat shock treatment on inseminated eggs at about 40° C. for 1.5 to 2.5 minutes within 25 to 35 minutes after insemination to obtain embryos and incubating the embryos in water to obtain offspring, selecting androgenetic offspring by testing the genomic DNA of the offspring by PCR for the presence or absence of genetic marker M1 having SEQ ID NO: 1 and SEQ ID NO: 2 and genetic marker M2 having SEQ ID NO: 3 and SEQ ID NO: 4 and comparing the marker pattern to that of the single female parent common carp and the single male parent common carp wherein selection of an offspring as androgenetic occurs when the genomic DNA of offspring comprises genetic markers M1, M2, or both, consistent with the markers of the single male parent common carp and does not comprise genetic markers M1, M2, or both, consistent with the markers of the single female parent common carp, cultivating the androgenetic offspring to sexual maturation to obtain androgenetic YY super-male common carp, confirming the androgenetic genotype of the obtained androgenetic YY super-male common carp by test cross using sperms of the sexually mature androgenetic offspring to fertilize eggs from normal female common carp, wherein obtaining from the test cross a population of sexually mature common carp comprising 100% XY male offspring confirms the androgenetic genotype of the obtained common carp.

2. A method for producing XY physiological female common carp, comprising:

providing eggs of a single female parent common carp in a cell culture medium, treating the eggs with UV irradiation, wherein the eggs are treated with a 30 W UV sterilization lamp with a wavelength of 254 nm at an irradiation distance of 24-28 cm for about 3.5 to 4.5 minutes, artificially inseminating the treated eggs with sperms of a single male parent common carp and performing a heat shock treatment on inseminated eggs at about 40° C. for 1.5 to 2.5 minutes within 25 to 35 minutes after insemination to obtain embryos and incubating the embryos in water to obtain offspring, selecting androgenetic offspring by testing the genomic DNA of the offspring by PCR for the presence or absence of genetic marker M1 having SEQ ID NO: 1 and SEQ ID NO: 2 and genetic marker M2 having SEQ ID NO: 3 and SEQ ID NO: 4 and comparing the marker pattern to that of the single female parent common carp and the single male parent common carp wherein selection of an offspring as androgenetic occurs when the genomic DNA of offspring comprises genetic markers M1, M2, or both, consistent with the markers of the single male parent common carp and does not comprise genetic markers M1, M2, or both, consistent with the markers of the single female parent common carp, cultivating the androgenetic offspring to sexual maturation to obtain androgenetic YY super-male common carp, confirming the androgenetic genotype of the obtained androgenetic YY super-male common carp by test cross using sperms of the sexually mature androgenetic offspring to fertilize eggs from normal female common carp, wherein obtaining from the test cross a population of sexually mature common carp comprising 100% XY male offspring confirms the androgenetic genotype of the obtained common carp, cultivating the XY male offspring of the confirmed androgenetic YY super-male common carp to 2 months old, feeding the cultivated XY male offspring with a sex reversal treatment for 3 months, wherein the sex reversal treatment is to feed the XY male offspring with feed mixed with estradiol at 200 mg/kg and Flutamide at 200 mg/kg twice daily, and feeding and growing the treated XY male offspring with normal feed to mature XY physiological female common carp.

3. The method for producing androgenetic YY super-male common carp according to claim 1, wherein the eggs of the single female parent common carp are dispersed and suspended in the cell culture medium at a concentration of about 1200 to 1800 eggs per 50 ml cell culture medium.

4. The method for producing XY physiological female common carp according to claim 2, wherein the eggs of the single female parent common carp are dispersed and suspended in the cell culture medium at a concentration of about 1200 to 1800 eggs per 50 ml cell culture medium.

* * * * *